US007386143B2

(12) United States Patent
Easter et al.

(10) Patent No.: US 7,386,143 B2
(45) Date of Patent: Jun. 10, 2008

(54) RETENTION APPARATUS FOR AN EXTERNAL PORTION OF A SEMI-IMPLANTABLE HEARING AID

(75) Inventors: James Roy Easter, Lyons, CO (US); Travis Rian Andrews, Boulder, CO (US); Peter Robert Mellers, Eaton, CO (US)

(73) Assignee: Otologics LLC, Boulder, CO (US)

( * ) Notice: Subject to any disclaimer, the term of this patent is extended or adjusted under 35 U.S.C. 154(b) by 866 days.

(21) Appl. No.: 10/678,959

(22) Filed: Oct. 2, 2003

(65) Prior Publication Data

US 2004/0133065 A1 Jul. 8, 2004

Related U.S. Application Data

(60) Provisional application No. 60/415,386, filed on Oct. 2, 2002.

(51) Int. Cl.
*H04R 25/00* (2006.01)
*A61N 1/00* (2006.01)

(52) U.S. Cl. .......................... 381/331; 600/25; 607/36; 607/57; 380/312; 380/322; 380/324

(58) Field of Classification Search .................. 600/25; 607/57, 36; 381/312, 314, 322–324, 326, 381/329, 331

See application file for complete search history.

(56) References Cited

U.S. PATENT DOCUMENTS

| | | | | |
|---|---|---|---|---|
| 4,606,329 | A | 8/1986 | Hough | 128/1 |
| 5,545,191 | A * | 8/1996 | Mann et al. | 607/57 |
| 6,178,353 | B1 * | 1/2001 | Griffith et al. | 607/61 |
| 6,275,736 | B1 * | 8/2001 | Kuzma et al. | 607/57 |
| 6,381,336 | B1 | 4/2002 | Lesinski et al. | 381/326 |
| 6,517,476 | B1 | 2/2003 | Bedoya et al. | 600/25 |
| 6,626,822 | B1 | 9/2003 | Jaeger et al. | 600/25 |

* cited by examiner

*Primary Examiner*—Wayne Young
*Assistant Examiner*—Dionne H Pendleton
(74) *Attorney, Agent, or Firm*—Marsh Fischmann & Breyfogle LLP

(57) ABSTRACT

A retention apparatus for a semi-implantable hearing aid. In one embodiment, the retention apparatus includes a first surface and a second surface. One of the first and second surfaces includes a first portion and a second portion having a rounded transition therebetween for interfacing with a patient's skin. The rounded transition of the interfacing surface of the retention apparatus functions to distribute pressure resulting from the mutual magnetic attraction between an externally located magnet and an implanted magnet to permit increased magnetic forces therebetween and maintenance of a desired separation between an external coil and implanted coil.

26 Claims, 9 Drawing Sheets

RETENTION APPARATUS FOR AN EXTERNAL PORTION OF A SEMI-IMPLANTABLE HEARING AID

RELATED APPLICATIONS

This patent application claims priority under 35 U.S.C Section 119 to U.S. Provisional Patent Application Ser. No. 60/415,386, that was filed on Oct. 2, 2002, and that is entitled "RETENTION APPARATUS FOR AN EXTERNAL PORTION OF A SEMI-IMPLANTABLE HEARING AID." The entire disclosure of U.S. Provisional Patent Application Ser. No. 60/415,386 is incorporated herein by reference.

FIELD OF THE INVENTION

The invention is related to the field of hearing aids, and in particular, to a retention apparatus for mounting and positioning an external portion of a semi-implantable hearing aid relative to a patient.

BACKGROUND OF THE INVENTION

Implantable hearing aids entail the subcutaneous positioning of some or all of various hearing augmentation componentry on or within a patient's skull, typically at locations proximal to the mastoid process. In a semi-implantable hearing aid, a microphone, signal processor, and transmitter may be externally located to receive, process, and inductively transmit a processed audio signal to an implanted receiver. The processed audio signal is provided to an implanted transducer, which stimulates a component of the auditory system to produce/enhance the sensation of sound for the patient.

In one example of a semi-implantable hearing aid, the implanted receiver is located beneath the skin of a patient, e.g. within the mastoid process, while the external transmitter is included in a housing detachably connectable to the patient proximate to the implanted receiver. In this characterization, the housing is connected to the patient via an implanted magnet oriented to produce a mutual attraction with a magnet located in the external housing. The external housing is typically positioned adjacent the implanted magnet on the patient's skull, e.g. behind the ear. The mutual attraction of the magnets serves to hold the external housing in place such that a desirable separation exists between a transmitting coil of the external transmitter and a receiving coil of the implanted receiver.

The desired separation is somewhat determined by the thickness and properties of the patient's skin separating the two magnets. As will be appreciated, since magnetic attractive force falls off rapidly with distance, in some cases the external housing may not be held securely against the skin of the patient. This in turn results in an undesirable separation or distance between the external and implanted coils. One solution to this problem is to use a stronger magnet(s) to connect the external housing. As will further be appreciated, however, the resulting pressure from the mutual attraction of the magnets may impair the circulation of blood in the capillaries of the patient's skin. Thus, it is desirable that the pressure applied on any part of the patient's skin be minimized to the extent possible. This often results in a tradeoff between avoiding pressure that may impair circulation and achieving a desired level of magnetic attraction, e.g. such that the external component is not held so loosely that an undesired coil separation exists.

As will also be appreciated, a tether including a means such as a clip for attaching to the patient, e.g. the patient's hair, may also be included on the external housing portion of the hearing aid. The tether functions as a safety link between the external housing and the patient to protect the external housing from falling and becoming damaged in the event that the magnetic attraction is broken during use.

SUMMARY OF THE INVENTION

In view of the foregoing, a primary object of the present invention is to improve mounting and positioning of the external portion of a semi-implantable hearing aid on a patient. Another object of the present invention is to provide a more secure attachment to the patient of the external portion. Another object of the present invention is to increase the magnetic attraction between the external housing and the implanted magnet while avoiding pressure that may impair circulation. A related object of the present invention is to more evenly distribute pressure applied on the patient's skin to reduce pressure concentration points between the external housing and internal magnet. Still yet another object of the present invention is to improve the attachment of the external portion while providing additional protection of the external portion in the event that the magnetic attraction is broken during use.

According to one aspect of the present invention, a retention apparatus is provided. In one embodiment, the retention apparatus is configured for juxtaposed positioning between the external portion of a semi-implantable hearing aid and the patient's skin. The retention apparatus includes a first surface to interface with the external portion, e.g. an external housing, and a second surface designed to interface with the patient's skin. In this regard, the second surface includes a first portion and a second portion with a rounded transition therebetween that provides a contoured shape to the patient's skin. The contoured shape is designed to distribute pressure on the skin resulting from the mutual magnetic attraction, thereby permitting an increased attractive force between the magnets to be applied while locating the transmitting coil a desired distance from the receiving coil.

According to one example of this embodiment, the contoured surface may be configured as a shallow dish-shaped structure that provides a radius at the contact portion with the patient's skin that is defined by a desired level of dishing in the patient's skin. In other words, the radius of the contoured surface is formed to achieve a certain amount of depression of the contoured surface into the patient's skin to achieve a desired coil separation while distributing pressure over the contact region to reduce localized pressures. This provides the advantage of permitting the generation of a stronger magnetic attraction, e.g. through use of a stronger magnet either implanted or in the external housing, to maintain a desired distance between the transmit and receive coils, as the pressure applied by the mutual magnetic attraction is distributed over the contact region.

In another embodiment of the retention apparatus, the retention apparatus may be a shallow dish-shaped receptacle that includes its own magnet. According to this characterization, the magnet of the retention apparatus functions to securely position the retention apparatus in juxtaposed relation to the external portion of the hearing aid. Additionally, the magnet of the retention apparatus operates to strengthen or augment the mutual magnetic attractive force between the external and internal portions of the hearing aid to ensure that the external portion is held securely against the patient's skin and the desired coil separation is maintained. In one example of this embodiment, the magnet may be internally housed within the shallow dish-shaped receptacle. According to this characterization, the radius of the dish surface may be maximized as a function of the size of the magnet and thickness of the retention apparatus. In other words, the radius formed is the maximum radius achievable given the constraints imposed by the size of the magnet and thickness of the retention apparatus.

In another embodiment of the retention apparatus, the retention apparatus may be a separate magnet that is magnetically connectable to a magnet within the external housing. According to one example of this embodiment, the separate magnet may further include an arcuate surface along the portion contacting the patient's skin to distribute pressure over the contact region.

It should also be noted that the above embodiments provide the additional functionality of permitting a small portion of the patient's hair to be retained between the retention apparatus and the external portion, e.g. housing, of the hearing aid to more securely retain the external portion of the hearing aid and provide a backup measure to prevent damage in the event that magnetic attraction between the internal and external portions is broken during use.

According to another aspect of the present invention, an external housing for containing at least one external component of a semi-implantable hearing aid device is provided. The present housing includes a shallow dish shaped surface for interfacing with the patient's skin. As with the retention apparatus the dish shaped surface of the present housing is configured to distribute pressure applied on the skin by the mutual magnetic attraction between the external and internal portions of the hearing aid device, thereby reducing localized pressures. In this regard, one or more magnets may also be included within the housing to provide a magnetic attraction with an implanted magnet and connect the housing to the patient.

According to another aspect of the present invention, a method of mounting and/or positioning an external portion of a semi-implantable hearing aid is provided.

According to another aspect of the present invention, a semi-implantable hearing aid device including one of the external housing or the retention apparatus of the above aspects is provided.

Additional aspects, advantages and applications of the present invention will be apparent to those skilled in the art upon consideration of the following.

DETAILED DESCRIPTION

Reference will now be made to the accompanying drawings, which at least assist in illustrating the various pertinent features of the present invention. In this regard, the following description is presented for purposes of illustration and description and is not intended to limit the invention to the form disclosed herein. Consequently, variations and modifications commensurate with the following teachings, and skill and knowledge of the relevant art, are within the scope of the present invention. The embodiments described herein are further intended to enable others skilled in the art to utilize the invention in such, or other embodiments and with various modifications required by the particular application (s) or use(s) of the present invention.

Figure 1:
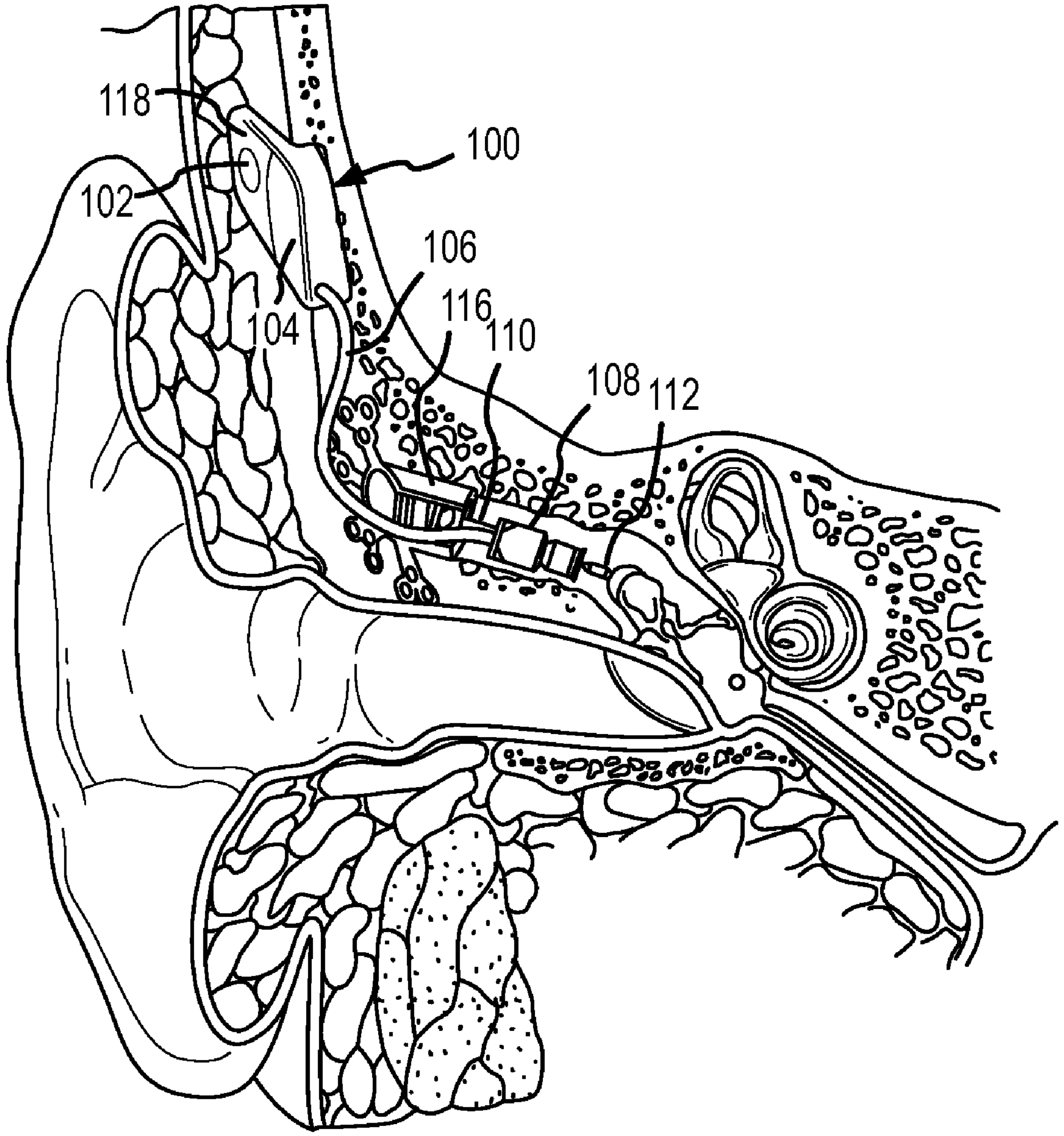
FIGS. 1 illustrates implantable componentry of a semi-implantable hearing aid.
Figure 2A:
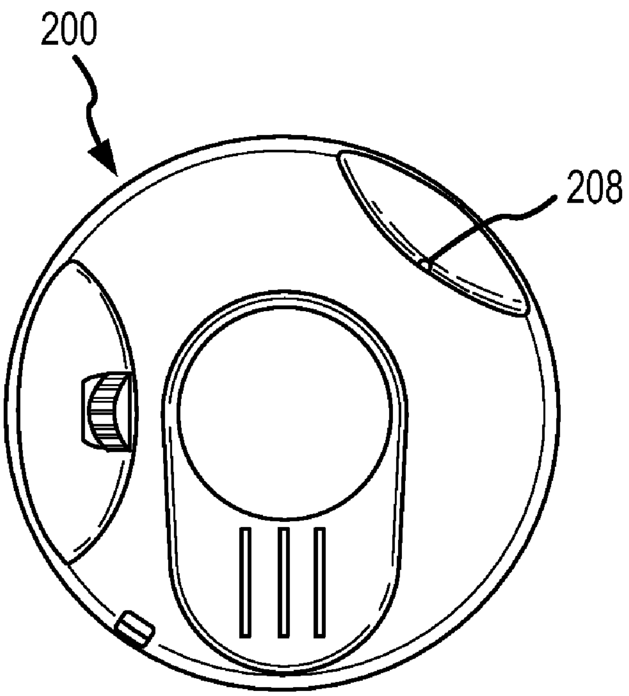
FIGS. 2*a-b* illustrates external componentry of a semi-implantable hearing aid.
Figure 2B:
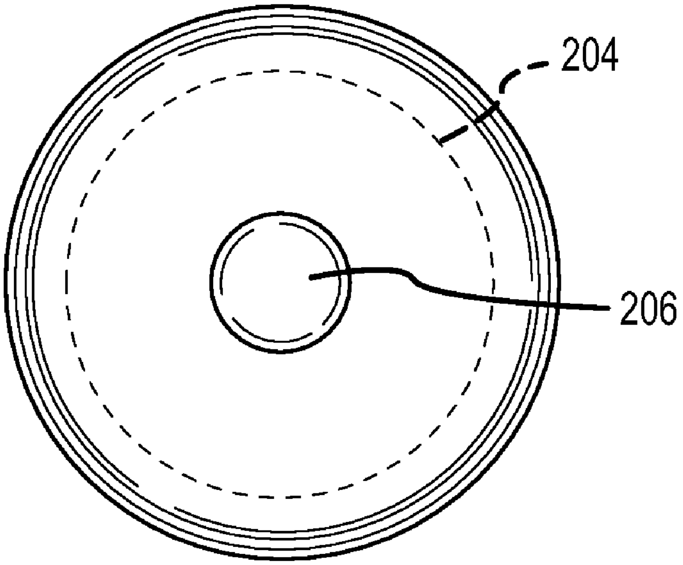
Figure 2C:
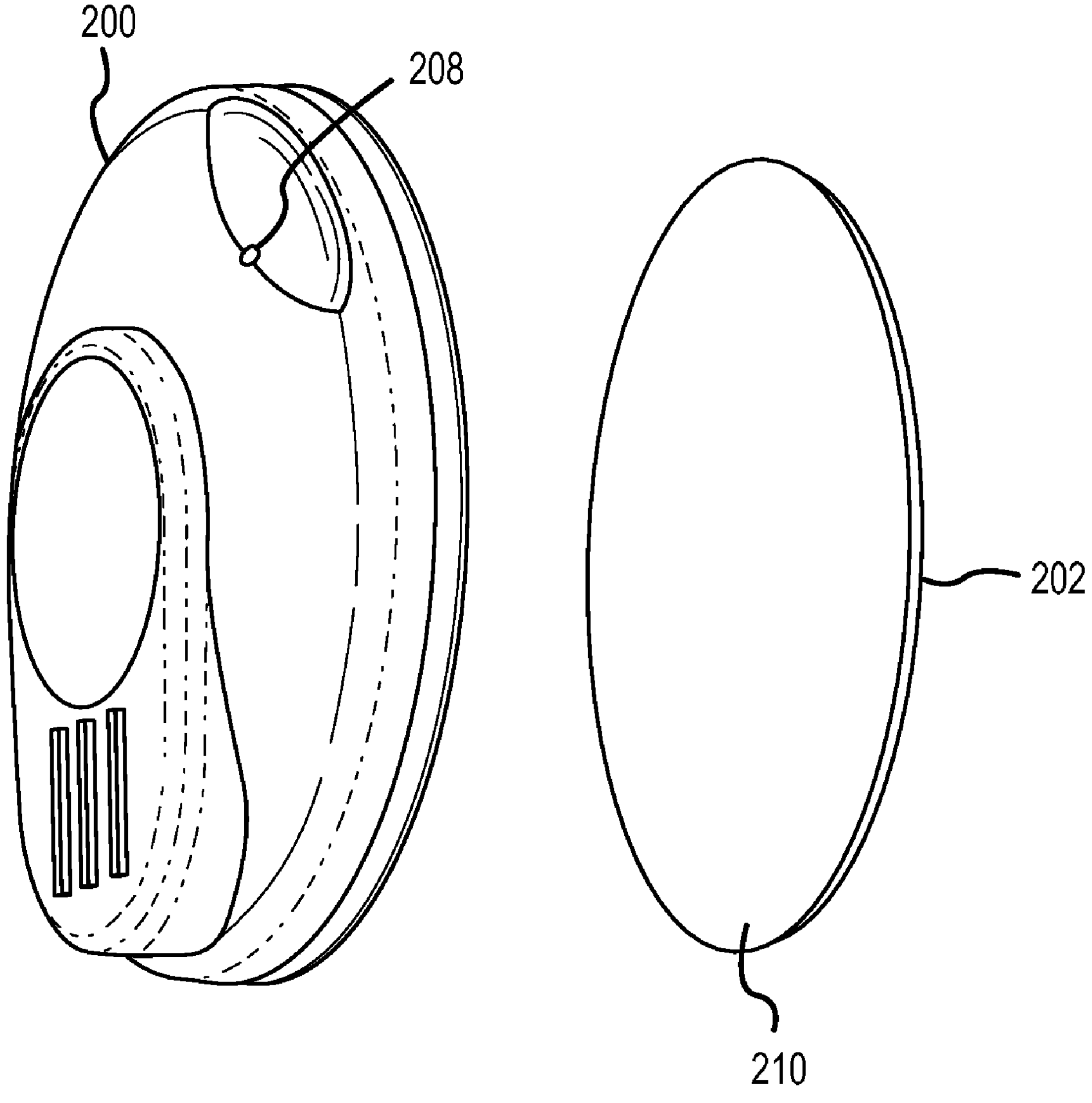
FIG. 2*c* illustrates an assembly view of the external componentry and a retention apparatus for a semi-implantable hearing aid.

FIGS. 1 and 2*a-b* illustrate one application of the present invention. The illustrated application includes a semi-implantable hearing aid system having implanted components shown in FIG. 1, and external components shown in FIGS. 2*a-b*. In the illustrated system, an implanted biocompatible housing 100 is located subcutaneously on a patient's skull. The housing 100 includes an RF signal receiver 118 (e.g. comprising a coil element) and a signal processor 104 (e.g. comprising processing circuitry and/or a microprocessor). The signal processor 104 is electrically interconnected via wire 106 to an electromechanical transducer 108. It should be noted that various other processing logic and/or circuitry may also be included in the housing 100 as a matter of design choice.

The transducer 108 is supportably connected to a positioning system 110, which in turn, is connected to a bone anchor 116 mounted within the patient's mastoid process (e.g. via a hole drilled through the skull). The electromechanical transducer 108 includes a vibratory member 112 for transmitting axial vibrations to a member of the ossicles of the patient (e.g. the incus).

Referring to FIGS. 2*a-b*, the semi-implantable system further includes an external housing 200 including a microphone 208, internally mounted speech signal processing (SSP) unit, and an RF signal transmitter 204 (e.g. comprising a coil element). During normal operation, acoustic signals are received at the microphone 208 and processed by the SSP unit within external housing 200. As will be appreciated, the SSP unit may utilize digital processing to provide frequency shaping, amplification, compression, and other signal conditioning, including conditioning based on patient specific fitting parameters. In turn, the SSP unit provides RF signals to the transmitter 204. Such RF signals may comprise carrier and processed acoustic drive signal portions. The RF signals are transcutaneously transmitted by the external transmitter 204 to the implanted receiver 118. As noted, the external transmitter 204 and implanted receiver 118 may each comprise coils for inductive coupling of signals therebetween.

Upon receipt of the RF signals, the implanted signal processor 104 processes the signals (e.g. via envelope detection circuitry) to provide a processed drive signal via wire 106 to the electromechanical transducer 108. The drive signals cause the vibratory member 112 to axially vibrate at acoustic frequencies to effect the desired sound sensation via mechanical stimulation of the ossicles of the patient.

The external housing 200 is configured for disposition behind the patient's ear in alignment with the implanted housing 100. According to this characterization, the external housing 200 and internal housing 100 each include magnets, 206 and 102, respectively, to achieve retentive juxtaposed positioning of the external housing 200 relative to the internal housing 100.

Figure 3:
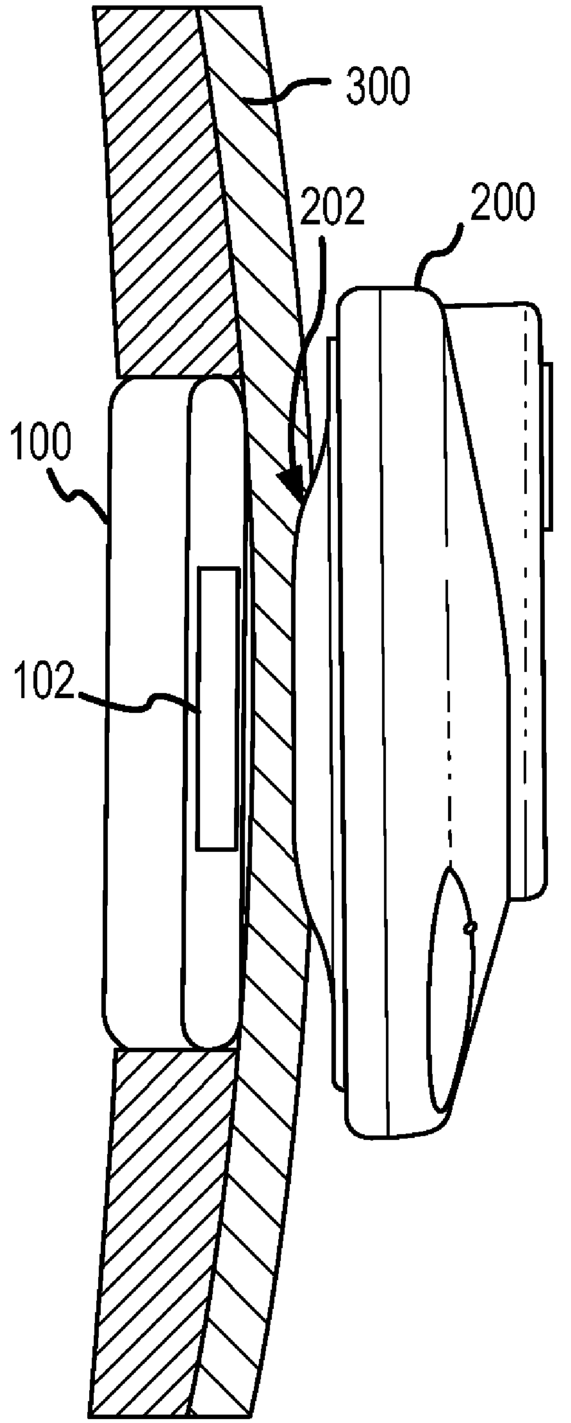
FIG. 3 illustrates the juxtaposed positioning of the external componentry and retention apparatus relative to the implanted componentry of a semi-implantable hearing aid device.
Figure 4:
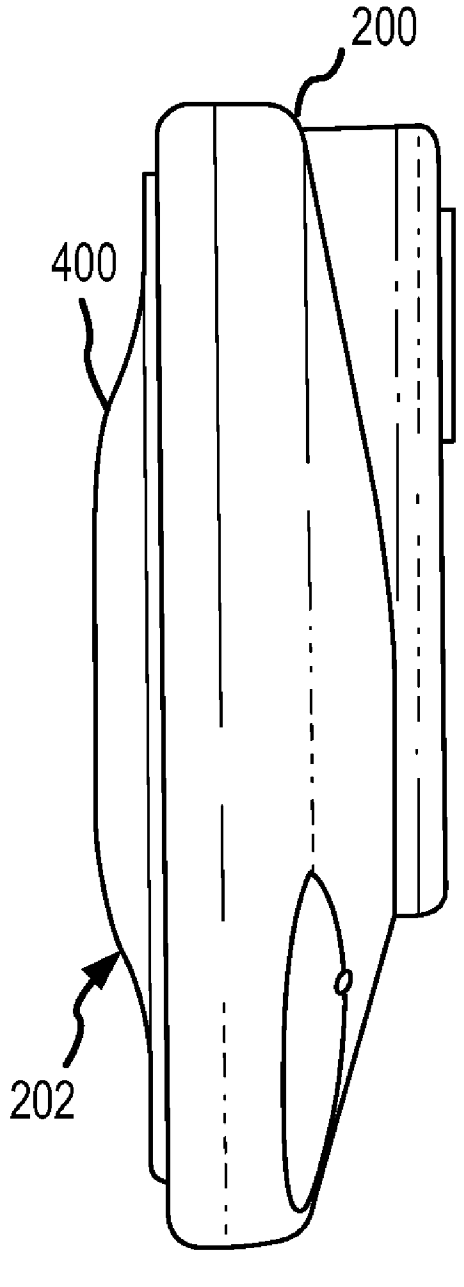
FIG. 4 illustrates an assembled view of the external componentry and retention apparatus for a semi-implantable hearing aid.

Referring to FIGS. 2*c*-4, to facilitate the retentive juxtaposed positioning of the external housing 200, the external portion of the hearing aid includes a retention apparatus 202. In one example, illustrated in FIG. 2*c*, the retention apparatus 202 is configured for disposition between the external housing 200 and the skin 300 of the patient. Alternatively, the retention apparatus 202 may be configured to operate with the hearing aid according to any appropriate method that facilitates the disposition of a shallow dish-shaped surface 400 adjacent the skin 300 of the patient. For instance, according to one characterization, the retention apparatus 202 may be an integrally formed part of the housing 200, as illustrated in FIG. 4. According to another characterization, the retention apparatus 202 may be a separate structure from the external housing 200, designed for disposition between the external housing 200 and the internal housing 100, as illustrated on FIG. 2*c*.

In the case where the retention apparatus 202 is a separate structure, the retention apparatus 202 is fabricated with a first surface 210 that forms a close interface when the retention apparatus 202 is mated with the housing 200 as shown in FIG. 3. In this regard, the retention apparatus 202 may be retained in position relative to the external housing 200 by any appropriate method. For instance, in one example, the retention apparatus 202 may be retained in position relative to the external housing 200 by the magnetic attraction between the pair of magnets 102 and 206 in the internal housing 100 and the external housing 200 respectively. In other words, the retention apparatus 202 is secured in a sandwiched position between the external housing 200 and internal housing 100 by the magnetic attraction between the magnets 102 and 206. In a similar manner, the retention apparatus 202 may be secured in position via other means, including without limitation, an adhesive bond or weld with the external housing 200.

Figure 5:
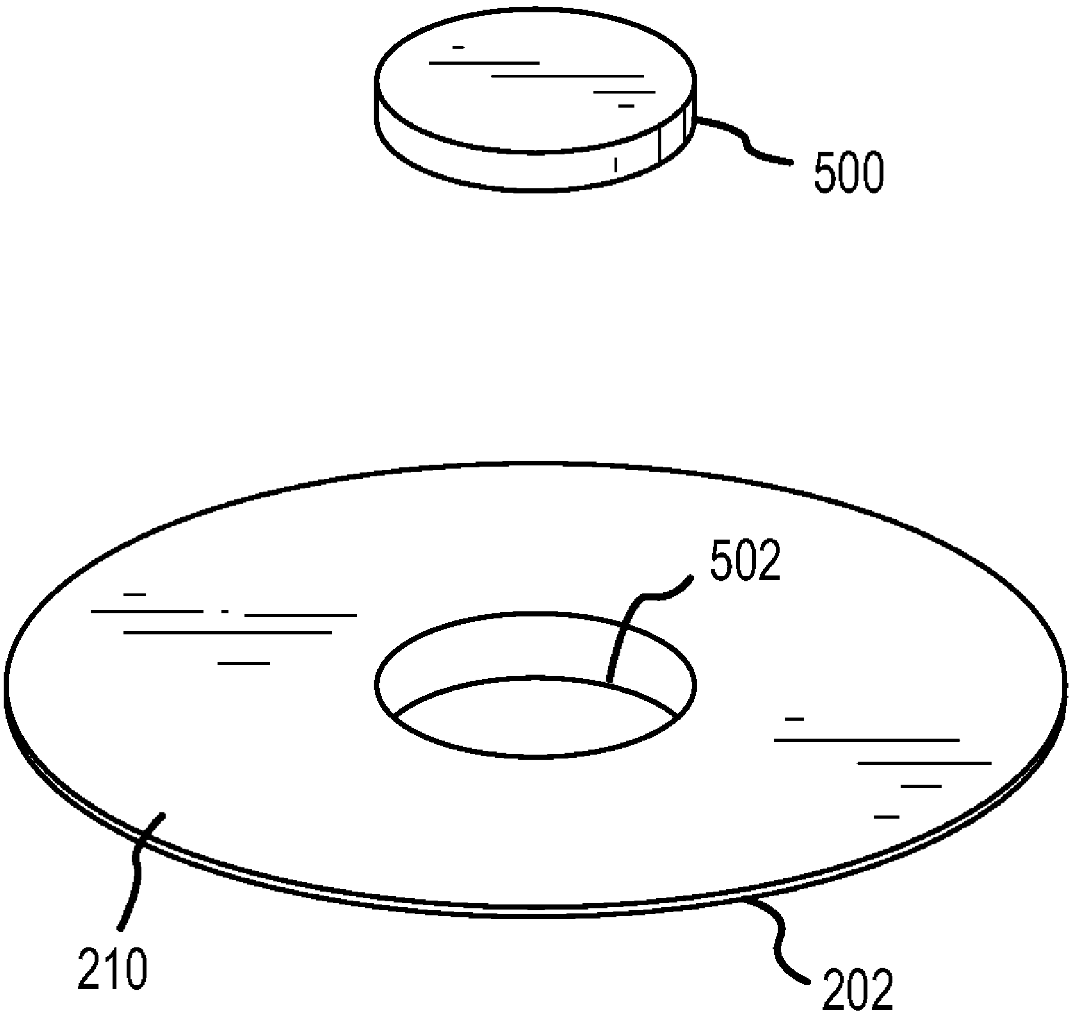
FIG. 5 illustrates an assembly view of a retention apparatus for a semi-implantable hearing aid.
Figure 6:
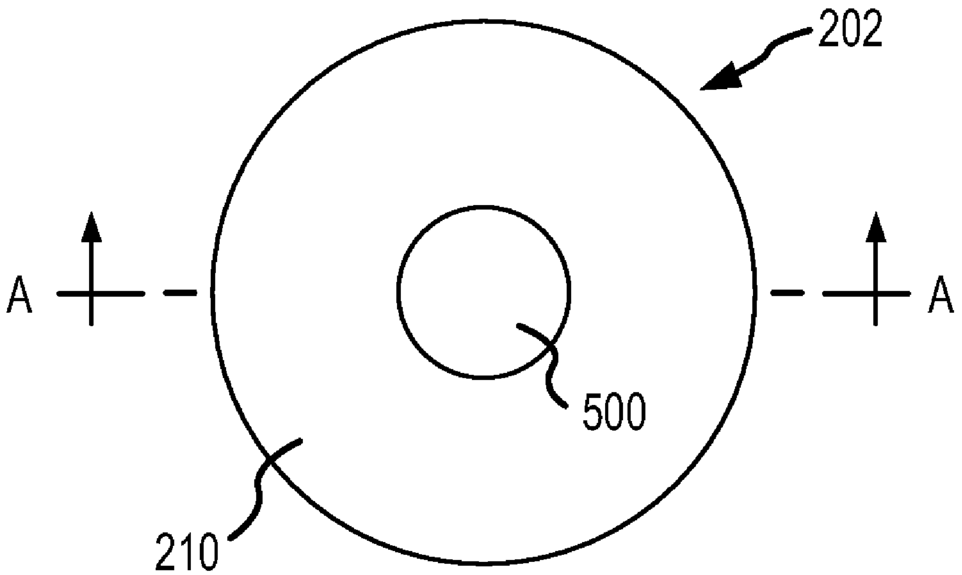
FIG. 6 illustrates a plan view of a retention apparatus for a semi-implantable hearing aid.
Figure 7:
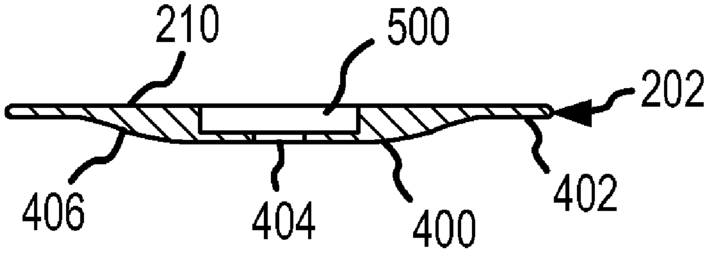
FIG. 7 illustrates a cross section view of the retention apparatus of FIG. 6.

In another example, illustrated in FIGS. 5-7, the retention apparatus 202 may be positionally secured relative to the external housing 200 by its own magnet 500. In this regard, the retention apparatus 202 is configured as a shallow dish-shaped receptacle including a pocket 502 for retaining the magnet 500. In this characterization, the magnet 500 may be secured within the pocket 502 via any appropriate method, including without limitation, an adhesive or compression fit between the magnet 500 and pocket 502. Advantageously, according to this characterization, the inclusion of the magnet 500 serves not only to facilitate the retentive juxtaposed position of the retention apparatus 202 and external housing 200, but also operates to strengthen or augment the mutual magnetic attraction between the external housing 200 and internal housing 100.

In any of the above embodiments, the retention apparatus 202 includes a second external surface 400. The external surface 400 includes a first portion 402 and a second portion 404 including a rounded transition 406 that provides a contoured shape to the patient's skin 300. The contoured shape is designed to distribute pressure exerted by the mutual attraction of the magnets, e.g. 102 and 206, to accommodate a stronger magnetic attraction, e.g. as a result of the addition of magnet 500 or the use of a stronger magnet 206 or 102. This in turn, permits the maintenance of a desired distance between the transmitting coil 204 and receiving coil 118. In other words, the contoured surface is designed to distribute pressure applied by the mutual magnetic attraction between the magnets 102 and 106 and/or 500 on the patient's skin 300 thereby permitting either use of stronger magnets for increased attraction or the accommodation of the increased attraction provided by the magnet 500. In this regard, the contoured surface may be configured to maximize the radius of any external corner presented to the patient's skin 300 such that the retention apparatus 202 distributes pressure over the contact region with the patient's skin 300 when the external portion of the hearing aid is mounted on the patient.

Figure 9:
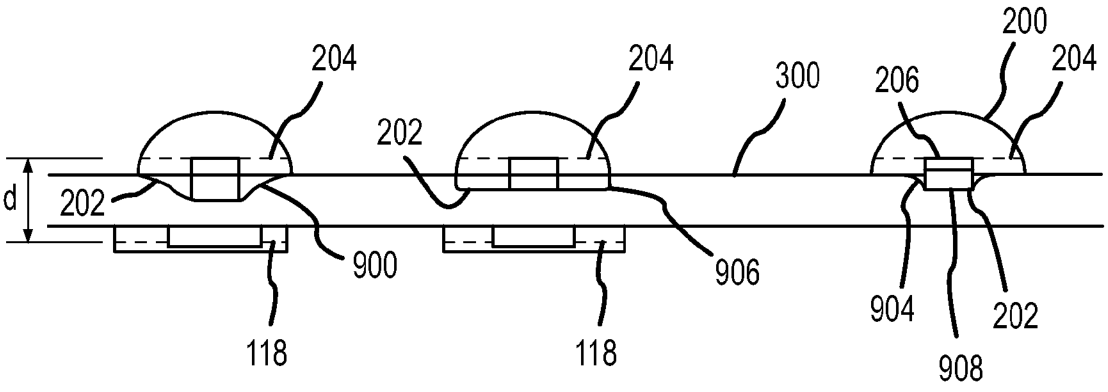
FIG. 9 illustrates various examples of an interface surface of the present retention apparatus

Referring to FIG. 9, according to one example of the retention apparatus 202, the contoured surface may be configured to provide a radius at the contact portion with the patient's skin 300 that is defined by a desired level of dishing in the patient's skin 300. To state it another way, the radius may include a range of radii that achieve a certain amount of depression of the contoured surface into the patient's skin 300 to achieve a desired separation between coils 204 and 118. The following three examples are set forth as an illustration of the above principle. In a first example, a minimum radius 904 may be provided. This in turn results in an increased mutual attraction between the magnets, e.g. 102 and 206 and/or 500, which in turn results in a reduced distance "d" between the coils 204 and 118. However, this also results in an increase in the amount of localized pressures, e.g. as the pressures are not distributed over as much area due to the sharper radius 904. In a second example, a radius 906 may be provided. The radius 906 results in a reduced attraction, which in turn results in an increased distance "d." However, this also results in a reduced amount of localized pressures, as the pressure is distributed over a greater area. In a third example, a radius 900 may be provided. The radius 900 results in an attraction that is greater than achieved with the radius 906 but less than achieved with the radius 904. Similarly, the resulting localized pressures are between those provided by the radius 904 and the radius 906.

The above-described principles provide the advantage of permitting a broad combination of magnetic strengths and radii to be utilized to accommodate differences in thickness and properties of different patient's skin such that a maximum level of comfort and functionality of the hearing aid system is achieved. Furthermore, it may be desirable to form the retention apparatus 202 in a manner that results in the thinnest possible configuration. In this regard, the radius 406 may be defined by the size of the magnet 500, where included, and the thickness of the first portion 402 of the retention apparatus 202, such that the radius is maximized according to these restraints.

Still referring to FIG. 9, in another embodiment of the present invention, the retention apparatus 202 may comprise a magnet, such as magnet 908, that magnetically mates with the magnet 206 within the housing 200. In a further example of this embodiment, the magnet 906 may include an arcuate radius, e.g. radius 904 provided over the region in contact with the patient's skin 300, to distribute resulting pressure from the mutual magnetic attraction.

Figure 8:
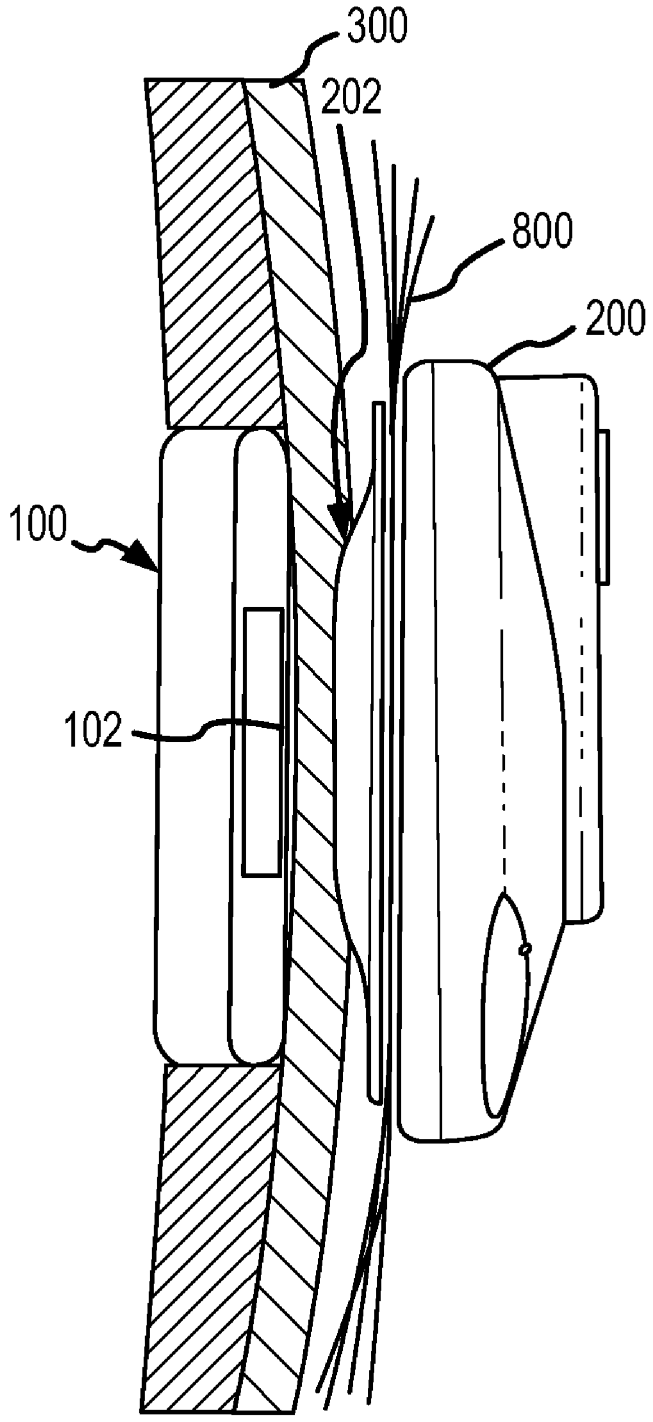
FIG. 8 illustrates another example of the juxtaposed positioning of the external componentry relative to the implanted componentry of a semi-implantable hearing aid device.

Referring to FIG. 8, to provide added security for the external portion of the hearing aid and to provide additional attachment of the external portion to the patient, the retention apparatus 202 also permits a small amount of the patient's hair 800 to be trapped between the juxtaposed retention apparatus 202 and external housing 200. Advantageously, this eliminates the need for additional hardware such as a tether and clip to provide added security to the external components of the hearing aid.

Additional features and advantages of the present invention will be apparent to those skilled in the art. For instance, in the above embodiments where the retention apparatus is a separate structure from the housing 200, the retention apparatus may be selectively provided to patients based on need. For instance, a conventional housing 200 and magnet 206 may be appropriate for some patients as a function of the properties, e.g. thickness of their skin, and/or activity level. In other patients, however, typically patients with thicker skin and/or that engage in physical activities such as contact sports where the housing 200 is subject to being knocked off, the retention apparatus may be provided as part of the hearing aid kit to enhance the connection between the external housing 200 and the patient. In another instance, wherein the retention apparatus includes the magnet 500 and or magnet 908, the polarity of the magnets prevents misconnection of the retention apparatus, e.g. the magnet 500 and or magnet 908 will only attract to the magnet 206 when properly oriented relative thereto. When improperly oriented the magnets will repel each other preventing misuse and or misconnection of the retention apparatus.

Those skilled in the art will appreciate variations of the above-described embodiments that fall within the scope of the invention. As a result, the invention is not limited to the specific examples and illustrations discussed above, but only by the following claims and their equivalents.

We claim:

1. A retention apparatus for an external housing of a semi-implantable hearing aid, comprising:

a disk member disposable between a patient's skin and an external housing, wherein the external housing contains at least one external component of the semi-implantable hearing aid, wherein at least one of said external housing and said disk member is retentively positionable relative to the patient's skin by magnetic attraction with an implantable magnet, wherein the disk member includes a first surface to form an interface with the external housing and a second surface to form an interface with the patient's skin, and wherein the second surface includes at least one rounded transition between a first and second portion of the second surface to provide a contoured shape to distribute pressure resulting from said magnetic attraction over an area of the patient's skin contacted by the second surface.

2. The retention apparatus of claim 1 wherein the contoured shape extends about a periphery of the area of the patient's skin contacted by the second surface.

3. The retention apparatus of claim 1 wherein the contoured shape is a shallow dish shape.

4. The retention apparatus of claim 1 wherein the rounded transition includes a predetermined radius to maintain a predetermined distance between a first coil located in the external housing and a second coil located subcutaneously on the patient.

5. The retention apparatus of claim 1 wherein the disk member is magnetic in nature.

6. The retention apparatus of claim 1 comprising:

a receptacle defined in the first surface for receiving a first magnet.

7. The retention apparatus of claim 6 wherein the disk member is retained in position relative to the external housing by the first magnet and a second magnet in the external housing.

8. The retention apparatus of claim 7 wherein the first surface forms a selectively connectable and disconnectable interface with the external housing with a portion of the patient's hair captured therebetween.

9. An external apparatus for a semi-implantable hearing aid, comprising:

a housing containing at least one component of the semi implantable hearing aid, wherein the housing includes an interface for retentive positioning of the housing on a patient's skin, wherein the interface includes a first surface having at least one rounded transition between a first portion and a second portion of the first surface; and a first magnet located within said housing for retentive positioning of the first surface in juxtaposed relation to and by magnetic attraction with an implanted magnet of the semi-implantable hearing aid, wherein the at least one rounded transition provides a contoured shape to distribute pressure resulting from the magnetic attraction over the an area of the patient's skin contacted by the first surface and wherein the interface is a separate structure from a first portion of the housing and includes a second surface for interfacing with the first portion of the housing, comprising: a receptacle defined in the second surface for receiving a second magnet.

10. The apparatus of claim 9 wherein the interface is an integral part of the housing.

11. The apparatus of claim 9 wherein the interface is a separate structure from a first portion of the housing and includes a second surface for interfacing with the first portion of the housing.

12. The apparatus of claim 11 wherein the second surface forms an interface with the first portion of the housing with a portion of the patient's hair captured therebetween.

13. The apparatus of claim 9 wherein the contoured shape extends about a periphery of the area of the patient's skin contacted by the first surface.

14. The apparatus of claim 9 wherein the contoured shape is a shallow dish shape.

15. The apparatus of claim 9 wherein the rounded transition includes a predetermined radius to define a predetermined distance between a first coil located in the housing and a second coil located subcutaneously on the patient.

16. The apparatus of claim 9 wherein the interface is magnetic in nature.

17. The apparatus of claim 9 wherein the interface is retained in position relative to the housing by the first and second magnets.

18. A method for mounting an external portion of a semi-implantable hearing aid on a patient, the method comprising:

providing a surface on the external portion that includes a contoured contact portion for contacting the patient's skin;

providing a radius of the contoured contact portion as a function of a magnetic attraction between an implanted magnet and an externally located magnet housed in said external portion; and disposing the external portion of the semi implantable hearing aid on the patient proximate the implanted magnet, wherein the external portion is retentively positioned by magnetic attraction of said externally located magnet with said implanted magnet, and wherein said contoured contact portion distributes pressure resulting from the magnetic attraction over an area of the patient's skin contacted by the external portion.

19. The method of claim 18 wherein the disposing step comprises:

locating a housing containing at least one component of the semi implantable hearing aid proximate the implanted magnet.

20. The method of claim 19 wherein the disposing step comprises:

prior to locating the housing, interfacing a disk shaped retention apparatus including the contoured contact portion with the housing; and locating the interfaced disk shaped retention apparatus and the housing on the patient proximate the implanted magnet.

21. The method of claim 20 retaining a portion of the patient's hair between the interfaced disk shaped retention apparatus and housing.

22. The method of claim 18 wherein the providing the radius step comprises:

providing one of a range of radii to achieve a predetermined depression of the contoured contact portion into the patient's skin to achieve a desired separation between a first coil located externally to the patient and a second coil located subcutaneously on the patient.

23. The method of claim 22 wherein the providing one of the range of radii step comprises:

selecting the one of the range of radii as a function of at least one of the magnetic attraction and the thickness of the patient's skin.

24. The method of claim 18 the method comprising:

varying one of the radius and the magnetic attraction to achieve the predetermined depression of the contoured contact portion into the patient's skin to achieve the desired separation between the first coil and the second coil.

25. The method of claim 18 wherein the method comprises:

providing one of a plurality of magnets having range of magnetic attractions to achieve a predetermined depression of the contoured contact portion into the patient's skin to achieve a desired separation between a first coil located externally to the patient and a second coil located subcutaneously on the patient; and locating the magnet in a receptacle of the external portion.

26. The method of claim 25 comprising:

retaining the disk shaped retention apparatus in a juxtaposed position relative to the housing using magnetic attraction between the disk shaped retention apparatus and the housing.

* * * * *